United States Patent [19]

Komatsu et al.

[11] 4,412,954
[45] Nov. 1, 1983

[54] PROCESS FOR PRODUCING 1,4,4A,9A-TETRAHYDROANTHRAQUINONE COMPOUND

[75] Inventors: Tatsuyoshi Komatsu, Kamakura; Kenji Usui, Nihonbashi, both of Japan

[73] Assignee: Kawasaki Kasei Chemicals Ltd., Tokyo, Japan

[21] Appl. No.: 283,174

[22] Filed: Jul. 14, 1981

[51] Int. Cl.³ ............................................. C07C 50/10
[52] U.S. Cl. .................................... 260/369; 260/385
[58] Field of Search ................ 260/369, 383, 384, 385

[56] References Cited

U.S. PATENT DOCUMENTS 3,870,730  3/1975  Scharfe et al. ...................... 260/369
4,284,576  8/1981  Schenk et al. ...................... 260/369

FOREIGN PATENT DOCUMENTS 56-43239  4/1981  Japan .

*Primary Examiner*—Thomas A. Waltz
*Attorney, Agent, or Firm*—Oblon, Fisher, Spivak, McClelland & Maier

[57] ABSTRACT

1,4,4a,9a-Tetrahydroanthraquinone compounds are produced by Diels-Alder reaction of 1,4-naphthoquinone with a conjugated diolefin in the 1,4,4a,9a-tetrahydroanthraquinone compound as a reaction medium.

2 Claims, No Drawings

PROCESS FOR PRODUCING 1,4,4A,9A-TETRAHYDROANTHRAQUINONE COMPOUND

BACKGROUND OF THE INVENTION

1. Field of the Invention

The present invention relates to a process for producing a 1,4,4a, 9a-tetrahydroanthraquinone compound which is useful as an intermediate of organic chemicals especially dyes, by reacting 1,4-naphthoquinone with a conjugated diolefin. More particularly, it relates to a process for producing 1,4,4a,9a-tetrahydroanthraquinone by reacting 1,4-naphthoquinone with a conjugated diolefin in a reaction medium of 1,4,4a,9a-tetrahydroanthraquinone.

2. Description of the Prior Art

In the production of a 1,4,4a,9a-tetrahydroanthraquinone compound (hereinafter referred to as THAQ compound) by the Diels-Alder reaction of 1,4-naphthoquinone (hereinafter referred to as NQ) with a conjugated diolefin, the reaction has been carried out in an inert medium, for example an aromatic hydrocarbon such as benzene, xylene and naphthalene. However, in order to complete the reaction, it is necessary to use more than equimole of a conjugated diolefin to NQ and to recover excess conjugated diolefin after the reaction. In the conventional process using an organic solvent, the conjugated diolefin has high affinity to the solvent and accordingly, the recovery of the conjugated diolefin has not been easy. When THAQ compound is obtained from the reaction mixture, the organic solvent should be separated from the reaction mixture including the organic solvent. A step of separation and recovery of the organic solvent such as distillation is required. Even though it is disilled in vacuum, the organic solvent is not easily separated and a portion thereof is remained. It has been difficult to completely separate the solvent.

SUMMARY OF THE INVENTION

It is an object of the present invention to provide a process for producing a 1,4,4a,9a-tetrahydroanthraquinone compound having high purity by a simple operation without difficulty for separating an organic solvent.

The foregoing and other objects of the present invention have been attained by a process for producing a 1,4,4a,9a-tetrahydroanthraquinone compound by Diels-Alder reaction of 1,4-naphthoquinone with a conjugated diolefin which comprises reacting them in the 1,4,4a,9a-tetrahydroanthraquinone compound as a reaction medium.

DETAILED DESCRIPTION OF THE PREFERRED EMBODIMENTS

It has been found the following fact:

(1) THAQ compound as the product is mostly liquid under a condition of Diels-Alder reaction of NQ with a conjugated diolefin.

(2) NQ is dissolved in the liquid THAQ compound.

(3) THAQ compound having high quality can be obtained at high yield, by feeding 1,3-butadiene in the form of gas or liquid into the liquid NQ under the reaction condition.

As a result, a novel process being different from the conventional process using an organic solvent has been found to complete the present invention.

The process of the present invention is characterized by producing THAQ in the substantial absence of the other organic solvent by using THAQ compound as the reaction medium in the production of THAQ compound by the Diels-Alder reaction of NQ with a conjugated diolefin.

Moreover, it is characterized by producing THAQ by reacting NQ with a conjugated diolefin in the liquid corresponding THAQ compound; discharging a portion of the reaction product substantially made of THAQ compound in the form of liquid or solid; recycling the portion of the reaction product as a reaction medium; and separating a residue of the reaction product made of THAQ and derivatives thereof as the intermediates for digesting assistants for pulp, dyes and agricultural chemicals and anthraquinone and dihydroanthraquinone derivatives.

The conjugated diolefins used in the present invention can be (a) 1,3-butadiene and also substituted butadienes such as (b) isoprene, (c) piperylene, (d) 2-butylbutadiene, (e) 2-methoxybutadiene, (f) 2-phenylbutadiene, (g) 2,3-dimethylbutadiene, (h) chloroprene and (i) 2-bromobutadiene, and conjugated cyclodiolefins such as (j) cyclopentadiene and (k) 1,3-cyclohexadiene.

THAQ compounds obtained by the Diels-Alder reaction of NQ with a conjugated diolefin include the compounds corresponding to the conjugated diolefins: such as (a) THAQ, (b) 2-methyl-THAQ, (c) 1-methyl-THAQ, (d) 2-butyl-THAQ, (e) 2-methoxy-THAQ, (f) 2-phenyl-THAQ, (g) 2,3-dimethyl-THAQ, (h) 2-chloro-THAQ, (i) 2-bromo- THAQ, (j) 1,4-endomethylene-THAQ, and (k) 1,4-endoethylene-THAQ which have each melting point of up to about 180° C. and are effectively used for the process of the present invention.

The THAQ compound obtained by the reaction has a melting point of up to 250° C. preferably up to 180° C. especially up to 150° C., especially preferably up to 120° C.

In the Diels-Alder reaction of NQ with a conjugated diolefin, the reaction temperature is decided depending upon a kind and amount of the conjugated diolefin and a melting point of the corresponding THAQ compound and a concentration of NQ. The melting point of THAQ compounds are as follows: THAQ: about 105° C.; 2-methyl-THAQ: 81° C.; 2-isopropyl-THAQ: 86° C.; 2-butyl-THAQ, 63° C.; 2-chloro-THAQ: 76° C. Therefore, the reaction can be performed at about 100° C. in view of melting point falling caused by certain impurities. 2-phenyl-THAQ or 2-methoxy-THAQ has each melting point of about 143°–146° C. Thus, a reaction temperature is at least 145° C. usually about 150° C. even though certain melting point falling is considered.

The reaction temperature is higher than a melting point of the THAQ compound and is usually selected from a range of 80° to 250° C. preferably 100° to 180° C. especially 110° to 150° C. depending upon the condition of the reaction process. When the reaction temperature is too high, a velocity of the side reaction increases whereas when it is too low, a velocity of the main reaction is remarkably low. The reaction pressure is depending upon a reaction temperature and a kind and amount of the diolefin. The reaction pressure is up to 120 kg/cm$^2$G usually 1 to 30 kg/cm$^2$G preferably 3 to 20 kg/cm$^2$G.

When an amount of the conjugated diolefin is excess to NQ, the reaction is completed for a shorter time. When it is too much, it is not economical in view of an apparatus. A molar ratio of the conjugated diolefin to NQ is usually in a range of 1 to 20 preferably 1.1 to 10.

A reaction time is decided depending upon a kind and concentration of the conjugated diolefin and a reaction temperature. The optimum reaction time is usually in a range of 0.1 to 5 hours.

The process of the present invention can be carried out by a batch system; a semicontinuous system having series of batch reactors; and a continuous system using a pipe reactor.

The typical process of the present invention will be illustrated by one example using 1,3-butadiene.

A mixture of THAQ and NQ is heated at 120° C. and 1,3-butadiene in the form of liquid or gas is fed into the mixture under a reaction pressure of 6 kg/cm$^2$G. with stirring for 2.5 hours. After the reaction, excess 1,3-butadiene is recovered from the reaction mixture and the liquid THAQ is obtained without a purification. In usual, a portion of the reaction mixture is based as the reaction medium in the next reaction and the residue is used as a product, if necessary forming a flake or a powder thereof, or the residue is used as an intermediate in a production of anthraquinone or dihydroanthraquinone.

In the process of the present invention, THAQ can be substantially used as the reaction medium. THAQ is usually used at a ratio of 0.5 to 5 part to 1 part of NQ. In the other embodiment, NQ (a melting point of 125° C. usually 110° C.–120° C. because of impurities) is melted before the reaction and 1,3-butadiene is fed under the condition of the reaction and the reaction is completed in the presence of the resulting THAQ.

The THAQ compound obtained by the process of the present invention is used as an intermediate for anthraquinone derivatives which are important as intermediates for dyes. The anthraquinone derivatives can be obtained by the conventional air oxidation process. The anthraquinone derivatives having high quality can be obtained at high yield.

The THAQ compounds are used as intermediates for anthraquinone type dyes and pigments. Moreover, new demand as digesting assistants for pulp is increased. Thus, the industrial production of THAQ compounds is remarkably required.

The process of the present invention is remarkably effective for an industrial operation in view of the production of various THAQ compounds having high quality used for various fields by a simple step at high yield.

The present invention will be illustrated by certain examples and references in detail. In the examples, the terms "part" and "%" mean "part by weight" and "% by weight" otherwise specified.

EXAMPLE 1

Into an autoclave, 30.0 parts of THAQ and 31.6 parts of NQ were charged and heated and kept at 120° C. Liquid 1,3-butadiene was fed into the mixture under a pressure of 6 kg/cm$^2$ Gauge with stirring to perform the reaction at a constant temperature and a constant pressure. After the reaction for 3 hours, excess butadiene was discharged and the reaction product was cooled to room temperature. An amount of the reaction product was 72.3 parts. The reaction product contained 99.2% of THAQ. A portion of the reaction product made of THAQ (30 parts) was used as a reaction medium in the next reaction under the same condition. The same result was attained.

EXAMPLE 2

Into an autoclave, 30.0 parts of 2-methyl-THAQ and 31.6 parts of NQ were charged and heated and kept at 115° C. Liquid isoprene was fed into the mixture under a pressure of 6 kg/cm$^2$ Gauge with stirring to perform the reaction at a constant temperature and a constant pressure. After the reaction for 3.5 hours, the reaction mixture was heated to 120° C. to discharge excess isoprene, and the reaction product was cooled to room temperature. An amount of the reaction product was 75.0 parts. The reaction product contained 98.5% of 2-methyl-THAQ. A portion of the reaction product made of 2-methyl-THAQ (30 parts) was used as a reaction medium in the next reaction under the same condition. The same result was attained.

REFERENCE EXAMPLE

Into an autoclave, 158 parts of NQ was charged and heated and kept at 125° C. Liquid 1,3-butadiene was fed into the mixture under a pressure of 6 kg/cm$^2$ Gauge with stirring to perform the reaction at a constant temperature and a constant pressure. After the reaction for 3 hours, excess 1,3-butadiene was discharged and the reaction product was cooled to room temperature. An amount of the reaction product was 212 parts. The reaction product contained 99.0% of THAQ.

We claim:

1. A process for producing a 1,4,4a,9a-tetrahydroanthraquinone compound which consists essentially of reacting by Diels-Alder reaction 1,4-naphthoquinone with a conjugated diolefin in 1,4,4a,9a-tetrahydroanthraquinone compound as a reaction medium in substantial absence of other organic solvent and wherein the amount of said tetrahydroanthraquinone is at a ratio of 0.5 to 5 parts by weight per part of naphthoquinone.

2. The process according to claim 1 wherein said reaction of 1,4-naphthoquinone with a conjugated diolefin compound is carried out in a liquid 1,4,4a,9a-tetrahydroanthraquinone compound and a portion of the resulting reaction product made of 1,4,4a,9a-tetrahydroanthraquinone compound is recycled as a reaction medium in the next reaction and a residue is separated as a product.

* * * * *